(12) United States Patent
Legen et al.

(10) Patent No.: US 8,592,490 B2
(45) Date of Patent: Nov. 26, 2013

(54) SELF-MICROEMULSIFYING DRUG DELIVERY SYSTEMS

(75) Inventors: Igor Legen, Grosuplje (SI); Janez Kerc, Ljubljana (SI); Polona Jurkovic, Ljubljana (SI)

(73) Assignee: LEK Pharmaceuticals D.D., Ljubljana (SI)

( * ) Notice: Subject to any disclaimer, the term of this patent is extended or adjusted under 35 U.S.C. 154(b) by 742 days.

(21) Appl. No.: 12/521,386

(22) PCT Filed: Dec. 14, 2007

(86) PCT No.: PCT/EP2007/063985
§ 371 (c)(1),
(2), (4) Date: Sep. 15, 2010

(87) PCT Pub. No.: WO2008/077823
PCT Pub. Date: Jul. 3, 2008

(65) Prior Publication Data
US 2010/0331356 A1 Dec. 30, 2010

(30) Foreign Application Priority Data
Dec. 27, 2006 (EP) .................... 06127228

(51) Int. Cl.
*A61K 9/00* (2006.01)
*A61K 9/107* (2006.01)
*A61K 9/16* (2006.01)
*A61K 47/00* (2006.01)

(52) U.S. Cl.
USPC ........... 514/784; 514/786; 514/937; 424/400; 424/455

(58) Field of Classification Search
USPC .................. 514/784, 786, 937; 424/400, 455
See application file for complete search history.

(56) References Cited

U.S. PATENT DOCUMENTS

| 5,645,856 A * | 7/1997 | Lacy et al. .................... 424/455 |
| 5,688,761 A | 11/1997 | Owen et al. |
| 2003/0022944 A1 | 1/2003 | Gumkowski et al. |
| 2005/0079145 A1 | 4/2005 | Constantinides et al. |

FOREIGN PATENT DOCUMENTS

| WO | WO 93/02664 A | 2/1993 |
| WO | WO 94/08605 A | 4/1994 |
| WO | WO 94/08610 A | 4/1994 |
| WO | WO 95/14037 A | 5/1995 |
| WO | WO 95/24893 A | 9/1995 |
| WO | WO 97/40823 A | 11/1997 |
| WO | WO 99/29316 A | 6/1999 |
| WO | WO 01/01960 A | 1/2001 |
| WO | WO 03/00295 A | 1/2003 |

* cited by examiner

*Primary Examiner* — Mina Haghighatian
(74) *Attorney, Agent, or Firm* — Arent Fox LLP (57) ABSTRACT

Self-microemulsifying drug delivery systems and microemulsions used to enhance the solubility of pharmaceutical ingredients comprising a polyoxyethylene sorbitan fatty acid ester emulsifier; a fatty acid ester co-emulsifier and an oil.

8 Claims, 4 Drawing Sheets

SELF-MICROEMULSIFYING DRUG DELIVERY SYSTEMS

This application is the National Stage of International Application No. PCT/EP2007/063985, filed Dec. 14, 2007, which claims benefit under 35 U.S.C. 119(a)-(d) or (f) or 365(b) of foreign application EP 06127228.2, filed on Dec. 27, 2006, the contents of which are incorporated herein by reference in their entirety.

FIELD OF THE INVENTION

The present invention relates to self-microemulsifying drug delivery systems and microemulsions. These systems can be used to enhance the solubility of pharmaceutical ingredients so are advantageous in the medical field. Accordingly, the invention also relates to a pharmaceutical composition and a method of making such a composition. Thus the invention relates to liquid based surfactant pharmaceutical systems and methods for conversion of these liquid systems in solid state.

BACKGROUND OF THE INVENTION

The design and development of new drug delivery systems with the intention of enhancing the efficacy of existing drugs is an ongoing process in the pharmaceutical industry. Several drugs demonstrate low bioavailability because of poor dissolution in physiological fluids as well as poor permeability. There are many types of drug delivery systems that have been developed to try to address this problem.

Candesartan cilexetil, is an example of a poorly soluble drug where the in vitro and in vivo dissolution strongly affects the efficacy. A classical approach to increase the solubility of poorly water-soluble drugs is micronisation of the drug by means of a mechanical manipulation (i.e. pulverizing the drug into particles of a few microns in diameter).

This approach is not appropriate for candesartan cilexetil, because any mechanical stress applied to the crystals of candesartan cilexetil leads to deterioration of the crystal structure and/or partial or complete (if mechanical stress is long enough) amorphisation, resulting in decreased stability. For example, when micronized candesartan cilexetil with d(0.9) =5 μm is subjected to 40° C. and 75% humidity for 1 month the impurities changed from 0.33% to 0.85%, compared to 0.19% and 0.10% for the unmicronised sample.

Therefore, it is desirable to provide a drug delivery system which does not damage the crystal structure of the drug.

One approach is the use of emulsion and in particular microemulsion systems and self-microemulsifying drug delivery systems (SMEDDS). Such systems have potential because of their improved drug solubilization and are able to enhance the bioavailability of poorly water-soluble drugs through solubilization in the excipient matrix or interface and dispersion in the gastrointestinal tract.

However, there are several disadvantages of traditional emulsions, microemulsions and SMEDDS. One is their liquid or semi-liquid/semi-solid state. This presents difficulties in proper dosing for peroral administration.

SMEDDS form a microemulsion on addition of water, either during manufacturing of a pharmaceutical composition or by a medical professional or the patient prior to use, or in vivo. A further challenge for these systems is that it is difficult to precisely control the amount of water that is added to the SMEDDS, particularly when this happens in vivo. Therefore, there is a need for a SMEDDS that forms a microemulsion and remains as a microemulsion (rather than a emulsions which is less stable) on addition of any quantity of water.

The present invention aims to provide drug delivery systems which can advantageously be used to enhance the solubility of pharmaceutical ingredients, particularly poorly-soluble drugs where the dissolution strongly affects the efficacy. The aim is to provide drug delivery systems that include liquid based surfactant systems in the solid state form, prepared in the way that preserves all elementary benefits of the original liquid based surfactant systems, that is improvement of poor drug solubility.

It is believed that the aim thus achieved is also to provide drug delivery systems that are stable over a long period of time and on addition of any amount of water and are suitable for oral administration.

SUMMARY OF THE INVENTION

According to a first aspect, the present invention provides a self-microemulsifying drug delivery system comprising
  (i) a polyoxyethylene sorbitan fatty acid ester emulsifier;
  (ii) a co-emulsifier selected from glyceryl mono- or di-fatty acid esters of $C_6$-$C_{18}$ fatty acids; and
  (iii) an oil, selected from $C_6$-$C_{12}$ fatty acid triglycerides;
  wherein the polyoxyethylene sorbitan fatty acid ester emulsifier (i) and co-emulsifier (ii) are present in a ratio by weight of between 1:1 and 4:1 and,
  the emulsifier and co-emulsifier, (i) (ii) and oil (iii) are present in a ratio by weight of between 4:1 and 10000:1.

According to a second aspect, the present invention provides a microemulsion. This can either be a microemulsions that is obtainable by providing a self-microemulsifying drug delivery system according to the first aspect of the invention and adding water, or a microemulsions that can be formed from the polyoxyethylene sorbitan fatty acid ester emulsifier (i) and co-emulsifier (ii) present in a ratio by weight of between 1:1 and 4:1 and oil, selected from $C_6$-$C_{12}$ fatty acid triglycerides.

According to a third aspect, the present invention provides a solid pharmaceutical composition comprising a pharmaceutically active ingredient and either
  a) a self-microemulsifying drug delivery system comprising
    (i) a polyoxyethylene sorbitan fatty acid ester emulsifier;
    (ii) a co-emulsifier selected from glyceryl mono- or di-fatty acid esters of $C_6$-$C_{18}$ fatty acids; and
    (iii) an oil, selected from $C_6$-$C_{12}$ fatty acid triglycerides;
    wherein the polyoxyethylene sorbitan fatty acid ester emulsifier (i) and co-emulsifier (ii) are present in a ratio by weight of between 1:1 and 8:1 and
    the emulsifier and co-emulsifier, (i) (ii) and oil (iii) are present in a ratio by weight of between 1:10 and 10 0000:1, or
  b) a microemulsion comprising
    (i) a polyoxyethylene sorbitan fatty acid ester emulsifier;
    (ii) a co-emulsifier selected from glyceryl mono- or di-fatty acid esters of $C_6$-$C_{18}$ fatty acids;
    (iii) an oil, selected from $C_6$-$C_{12}$ fatty acid triglycerides;
    wherein the polyoxyethylene sorbitan fatty acid ester emulsifier (i) and co-emulsifier (ii) are present in a ratio by weight of between 1:1 and 8:1 and
    wherein the emulsifier and co-emulsifier, (i)+(ii) and oil (iii) are present in a ratio by weight of between 1:10 and 10 000:1; and
    (iv) water.

According to a fourth aspect, the present invention relates to the use of a self-microemulsifying drug delivery system according to the first aspect of the invention to enhance the solubility by a factor of three of a poorly soluble pharmaceutically active ingredient which has a solubility of less than 0.1 g of pharmaceutically active ingredient in 1 ml of water at 37° C.

According to a fifth aspect, the present invention provides a method of preparing a solid oral pharmaceutical composition comprising the steps of:
a) forming a self-microemulsifying drug delivery system comprising
   (i) a polyoxyethylene sorbitan fatty acid ester emulsifier;
   (ii) a co-emulsifier selected from glyceryl mono- or di-fatty acid esters of $C_6$-$C_{18}$ fatty acids; and
   (iii) an oil, selected from $C_6$-$C_{12}$ fatty acid triglycerides;
   wherein the polyoxyethylene sorbitan fatty acid ester emulsifier (i) and co-emulsifier (ii) are present in a ratio by weight of between 1:1 and 8:1 and the emulsifier and co-emulsifier, (i)+(ii) and oil (iii) are present in a ratio by weight of between 1:10 and 10 000:1; or
b) forming a microemulsions comprising
   (i) a polyoxyethylene sorbitan fatty acid ester emulsifier;
   (ii) a co-emulsifier selected from glyceryl mono- or di-fatty acid esters of $C_6$-$C_{18}$ fatty acids; and
   (iii) an oil, selected from $C_6$-$C_{12}$ fatty acid triglycerides;
   wherein the polyoxyethylene sorbitan fatty acid ester emulsifier (i) and co-emulsifier (ii) are present in a ratio by weight of between 1:1 and 8:1, and
c) adding a pharmaceutically active ingredient to the self-microemulsifying drug delivery system formed in step a) or the microemulsion formed in step b) to form a pharmaceutical composition; and
d) solidifying the pharmaceutical composition formed in step c) to form a solid oral pharmaceutical composition.

According to a sixth aspect, the present invention relates to the use of a self-microemulsifying drug delivery system according to the first aspect of the invention or a microemulsion according to the second aspect of the invention, to administer a pharmaceutically active ingredient to a patient.

All aspects of the invention essentially comprise a self-microemulsifying drug delivery system (SMEDDS) or a microemulsion which comprises three components, an emulsifier, a co-emulsifier and oil. In the invention, the components and their relative amounts have been selected so as to provide a SMEDDS which produces a microemulsion on addition of wide range of amounts of water. The SMEDDS of the present invention also exhibit improved drug solubilization, long shelf life, and ease of preparation.

The SMEDDS of the invention is advantageously used in pharmaceutical compositions to improve the solubility of poorly soluble drugs such as, according to a preferred embodiment, candesartan cilexetil, celecoxib, eprosartan mesylate, sirolimus or lercanidipine HCl.

The SMEDDS is converted into solid state thereby overcoming the problems associated with dosing liquid or semi-liquid compositions. Solid state emulsion systems comprise liquid based systems (emulsions, microemulsions or self microemulsifying systems) that are converted into solid state by spray drying, adsorption or stabilization with solid support. They are in the form of free flowing powder or granulate, which can be further filled in hard capsules or compressed into tablets.

Microemulsions or self microemulsifying systems according to the invention in solid state strongly increase the solubility of candesartan cilexetil without changing its crystal structure. The same effect can be expected also for other drugs (for example celecoxib, eprosartan mesylate, sirolimus and lercanidipine HCl).

According to a preferred embodiment of all aspects of the invention, the polyoxyethylene sorbitan fatty acid ester emulsifier is Polysorbate 80 (as polyoxyethylene 20 sorbitan monooleate). Polysorbate 80 (polyoxyethylene 20 sorbitan monooleate) is preferred over other polyoxyethylene sorbitan fatty acid esters such as Polysorbate 60 (polyoxyethylene 20 sorbitan monostearate) as it produces a better microemulsion. This is believed to be related to the fact that Polysorbate 80 (polyoxyethylene 20 sorbitan monooleate) is made from oleinic acid (rather than stearic acid as is the case in Polysorbate 60 (polyoxyethylene 20 sorbitan monostearate) and has a double bond in the lipophilic region. It is believed that the double bond means that Polysorbate 80 (polyoxyethylene 20 sorbitan monooleate) is particularly flexible and hence suited to forming stable emulsions.

It is essential in the present invention that the ester emulsifier (i) and co-emulsifier (ii) are present in a ratio by weight of between 1:1 and 8:1, preferably and essentially in some embodiments, between 1:1 and 4:1. Within this range of ratios, microemulsions that are stable on addition of any amount of water can be made. In the most preferred embodiment, the polyoxyethylene sorbitan fatty acid ester emulsifier (i) and co-emulsifier (ii) are present in a ratio by weight of between 1:1 and 6:1 or 4:1, for example about 1:1, 2:1 or 4:1, preferably between 2.5:1 and 3.5:1, for example about 3:1. The preferred ratios define systems that have been found to be particularly good at improving the solubility of pharmaceutical ingredients and from which microemulsions are formed on addition of any amount of water.

Further, it is essential that the ratio by weight of emulsifier and co-emulsifier (total emulsifier), (i) (ii), to oil (iii), is at least 1:10, and in some embodiments is essentially at least 4:1. Preferably there is more total emulsifier than oil so the ratio is at least 1:1. The lower limit on the amounts of oil, is a ratio of 10000:1. The ratio by weight of emulsifier and co-emulsifier (total emulsifier (i)+(ii)), to oil (iii), is preferably in the range 1:4 to 10000:1, preferably about 1:1 to 1000:1, more preferably 4:1 to 100:1, most preferably 5:1 to 40:1.

According to the most preferred embodiment, the self-microemulsifying drug delivery system consists of caprylic/capric triglyceride as oil (hydrophobic) phase, Polysorbate 80 (polyoxyethylene 20 sorbitan monooleate) as emulsifier and glyceryl caprylate as coemulsifier, and is made into a microemulsion by addition of water as the hydrophilic phase.

DETAILED DESCRIPTION OF THE INVENTION

By microemulsion we mean a thermodynamically stable, transparent dispersions of oil phase and water phase stabilized by an interfacial film of emulsifier (also known as surfactant) molecules. In a microemulsion the dispersed phase consists of globules which are less than 100 nm across. In contrast, an emulsion which is not a microemulsion (referred to as a non-microemulsion) has bigger globules in the dispersed phase and is not thermodynamically stable so will separate over time (although separation may occur very slowly).

Self-microemulsifying systems are comprised of a mixture of oil and emulsifiers (otherwise known as surfactants) which form a microemulsion upon dilution with aqueous medium. The SMEDDS according to the invention form thermodynamically stable microemulsions after addition of any amount of water.

The present invention involves a self-microemulsifying drug delivery system which comprises as the emulsifier (i) a polyoxyethylene sorbitan fatty acid ester. As noted above, polyoxyethylene 20 sorbitan monooleate, which is also known as Polysorbate 80 (polyoxyethylene 20 sorbitan monooleate), is particularly useful in the present invention.

The present invention also includes a co-emulsifier (ii) selected from glyceryl mono- or di-fatty acid esters of $C_6$-$C_{18}$ fatty acids. It was surprisingly found that glyceryl mono- or di-fatty acid esters of $C_6$-$C_{18}$ fatty acids form microemulsions with polyoxyethylene sorbitan fatty acid ester and $C_6$-$C_{12}$ fatty acid triglycerides in very wide concentration range. Preferably co-emulsifier is (ii) selected from glyceryl mono- or di-fatty acid esters of $C_6$-$C_{12}$ fatty acids. Glyceryl caprylate (which is known commercially as Imwitor 308® (glyceryl mono caprylate) is preferred for use as the co-emulsifier and particularly good results have been obtained with the use of glyceryl caprylate in combination with Polysorbate 80 (polyoxyethylene 20 sorbitan monooleate).

The self-microemulsifying systems of the present invention also include an oil (iii), which is a $C_6$-$C_{12}$ fatty acid triglycerides. Medium chain triglycerides are generally known to form microemulsion easier than long chain triglycerides. In the preferred embodiment, a caprylic/capric triglyceride is used, (known commercially as Mygliol 812® (caprylic/capric triglyceride)).

Hence, the self-microemulsifying systems of the present invention include as the co-emulsifier (ii) mono- or di-glycerides and as the oil (iii) triglycerides having the chain length and being in the amounts as defined above. It is preferred that the self-microemulsifying systems of the present invention do not contain a significant level of glycerides (including mono-, di-, or triglycerides which do not meet the compositional requirements of (ii) or (iii). In particular, it is preferred that of the total amount of glycerides in the self-microemulsifying systems of the present invention, at least 90%, more preferably 95% or 99% and most preferably all are either co-emulsifiers according to (ii) (selected from glyceryl mono- or di-fatty acid esters of $C_6$-$C_{18}$ fatty acids, preferably $C_6$-$C_{12}$ fatty acids), or oils according to (iii) (which is a $C_6$-$C_{12}$ fatty acid triglycerides).

In preferred embodiments the self-microemulsifying systems of the present invention includes only emulsifier according to (i), a coemulsifier according to (ii), an oil according to (iii) in the defined proportions and has no further components. Hence, the self-microemulsifying drug delivery system consists of (i) the polyoxyethylene sorbitan fatty acid ester emulsifier, (ii) the co-emulsifier selected from glyceryl mono- or di-fatty acid esters of $C_6$-$C_{18}$ fatty acids, and (iii), the oil, selected from $C_6$-$C_{12}$ fatty acid triglycerides.

In preferred embodiments, there is more coemulsifier than oil. Preferably the ratio of coemulsifier (ii) to oil (iii) is at least 1.5:1, preferably 2:1, more preferably at least 3:1.

The present invention also relates to microemulsions which contain an emulsifier according to (i), a coemulsifier according to (ii), an oil according to (iii) and water (iv). In preferred embodiments, the water is part of an aqueous phase which comprises at least 50%, preferably at least 70%, 80%, 90%, or 99%, and most preferably is all water. In particular it is preferred that the aqueous phase does not contain certain components such as alcohols that can be harmful to patients, particularly those who have a liver condition. Accordingly, it is preferred that the aqueous phase contains no alcohols, particularly no ethanol. It is also preferred that the aqueous phase does not contain any polyethylene glycol.

The present invention also relates to a solid pharmaceutical composition comprising a pharmaceutically active ingredient and either a self-microemulsifying drug delivery system or a microemulsion. The composition can be made into solid form in any way, such as by any of the methods described below.

Any pharmaceutically active ingredient can be incorporated into the composition. However, the invention is particularly useful for the peroral administration of poorly soluble drugs, i.e., those that display low dissolution in physiological fluids, which may results in poor bioavailability. By poorly soluble we mean the ingredient has a solubility of less than 0.1 g/ml of water at 37° C., as defined for practically insoluble drugs in USP29. The solubility of the ingredient can be determined by any technique know from those skilled in the art (i.e. the excess of the ingredient is placed in the certain amount of water, mixed with the magnetic stirrer and measure the dissolved amount of ingredient by a suitable analytical technique).

The pharmaceutically active ingredient is usually dissolved or dispersed in the self-microemulsifying drug delivery system or the microemulsion and is normally present in the range 5-70%, preferably 10-20% by weight with respect to the self-microemulsifying drug delivery system.

In the preferred embodiments, the pharmaceutically active ingredient is candesartan cilexetil, celecoxib, eprosartan mesylate, sirolimus or lercanidipine hydrochloride.

Candesartan cilexetil is a potent, long-acting, selective angiotensin II type I receptor (AT1) antagonist beneficial for the treatment of hypertension. Candesartan cilexetil is completely hydrolyzed to the active drug candesartan during absorption from the gastrointestinal tract. Candesartan has the chemical name 3-((2'-(2H-tetrazol-5-yl)biphenyl-4-yl)methyl)-2-ethoxy-3H-benzo[d]imidazole-4-carboxylic acid. Candesartan cilexetil is a very poorly soluble drug with water solubility 0.5 μg/ml (at 37° C.) and less than 0.2 μg/ml in phosphate buffer pH=7.0 (at 37° C.) representing the pH in the human small intestine, which is a primary site of drug absorption.

The drug which is commerically known as Celecoxib is a non-steroidal anti-inflammatory drug (NSAID) used in the treatment of various diseases including osteoarthritis, rheumatoid arthritis, acute pain, painful menstruation and menstrual symptoms. The chemical name is 4-[5-(4-methylphenyl)-3-(trifluoromethyl)pyrazol-1-yl]benzenesulfonamide.

Eprosartan mesylate is an angiotensin II receptor antagonist used for the treatment of high blood pressure. The chemical name for Eprosartan is 4-[[2-butyl-5-(2-carboxy-3-thiophen-2-yl-prop-1-enyl)-imidazol-1-yl]methyl]benzoic acid.

Sirolimus is a relatively new immunosuppressant drug used to prevent rejection in organ transplantation, and is especially useful in kidney transplants. It is also known as rapamycin. The chemical name of sirolimus is [3S-[3R*[E(1S*, 3S*,4S*)],4S*,5R*,8S*,9E,12R*,14R*,15S*,16R*,18S*, 19S*,26aR*]]-,6,8,11,12,13,14,15,16,17,18,19,24,25,26, 26a-hexadecahydro-5,19-dihydroxy-3-[2-(4-hydroxyl-3-methoxycyclohexyl)-1-methylethenyl]-14,16-dimethoxy-4, 10, 12,18-tetramethyl-8-(2-propenyl)-15,19-epoxy-3H-pyrido[2,1-c][1,4]oxaazacyclotricosine-1,7,20,21 (4H,23H)-tetrone, monohydrate.

Lercanidipine is a calcium channel blocker administered as HCl salt. The chemical name of lercanidipine is methyl[2-(3, 3-diphenylpropyl-methyl-amino)-1,1-dimethyl-ethyl]2,6-dimethyl-4-(3-nitrophenyl)-1,4-dihydropyridine-3,5-dicarboxylate The SMEDDS is used in the invention to improve the solubility of pharmaceutical ingredients and in the third aspect of the invention is used to enhance the solubility by a factor of three of a poorly soluble pharmaceutically active ingredient which has a solubility of less than 0.1 g of pure pharmaceutically active ingredient in 1 ml of water at 37° C.

According to a fourth aspect, the invention relates to a method of making a solid composition. This involves the step of solidifying a pharmaceutical composition which comprises a SMEDDS or a microemulsion and a pharmaceutical ingredient. Preferably the composition is suitable for oral administration.

Conversion into solid state can be achieved by different means including the four methods set out below.

In the first case, a liquid surfactant based system comprising the emulsifier, coemulsifier, oil and optionally water was adsorbed on a solid support. The solid support is chosen from the different solid pharmaceutical excipients, for example: colloidal silicon dioxide, talc, microcrystalline cellulose, magnesium oxide, magnesium hydroxide, titanium dioxide, lactose and polyvinylpyrrolidone. Preferably colloidal silicon dioxide is used. The liquid surfactant based system was slowly added to colloidal silicon dioxide during continuous vigorous mixing to obtain a free flowing powder.

In the second case, the liquid surfactant based system was converted into a solid state by stabilization of individual emulsion phases with hydrophilic and hydrophobic solid supports. Preferably colloidal silicon dioxide and hydrophobic colloidal silicon dioxide are used. In general, colloidal silicon dioxide is hydrophilic. On contrary, hydrophobic colloidal silicon dioxide is, for example, colloidal silica treated with dimethyldichlorosilane. The water phase of the dispersion was adsorbed on a hydrophilic solid support by vigorous mixing and the oil phase of the dispersion was adsorbed on a hydrophobic solid support also by vigorous mixing. Afterwards, solid state water phase, solid state oil phase and emulsifier mixture were mixed to obtain a free flowing powder.

In the third case, the liquid surfactant based system was incorporated in a polyethylene glycol dispersion. Polyethylene glycols of different molecular weights can be used, but preferably polyethylene glycol 6000 is used. Polyethylene glycol was melted in a water bath at 65° C. The self microemulsifying system was mixed with melted polyethylene glycol 6000. The obtained mixture was rapidly solidified in an ice bath. The solidified composition was pulverized and sieved to form a granulate which was put into hard capsules.

In the fourth case, the liquid surfactant based system was spray dried on a solid support. Different pharmaceutical excipients can be used as a solid support, for example: sugars such as lactose, maltose, fructose, dextran, glucose; sugar alcohols such as sorbitol, maltitol; polyvinylpyrrolidone (PVP), polyvinyl alcohol, low viscosity polymers such as low viscosity hydroxypropyl cellulose, colloidal silicon dioxide. Most preferably polyvinylpyrrolidone or lactose are used. The solid support was dissolved in water. This solution was mixed with the self microemulsifying system. The obtained dispersion was spray dried in a spray drying system. The resultant powder was put into hard capsules or compressed in tablets.

The point on the phase diagrams labelled EMULSIFIER: COEMULSIFIER (upper angle) represents a system which comprises 100% total emulsifier (i.e. emulsifier and coemulsifier), the point labelled OIL represents a system which comprises 100% oil and the point labelled WATER represents a system which comprises 100% water. EMULSIFIER is referred also to as (i), COEMULSIFIER as (ii) and oil as (iii)

The line from upper triangle to lower right triangle represents a SMEDDS, and points on this line represent different ratios of (EMULSIFIER:COEMULSIFIER): OIL. E.g. a point which lies at one quarter from upper angle to lower right angle represents a composition having 80% of (EMULSIFIER:COEMULSIFIER) and 20% of OIL thus having ratio (i)+(ii):(iii) 4; 1.

In all cases the experiments were carried out using Polysorbate 80 (polyoxyethylene 20 sorbitan monooleate) as the emulsifier, glyceryl caprylate (Imwitor 308® (glyceryl mono caprylate)) as the coemulsifier, caprylic/capric triglyceride (Mygliol 812® (caprylic/capric triglyceride)) as the oil and water as the hydrophilic phase.

Figure 1:
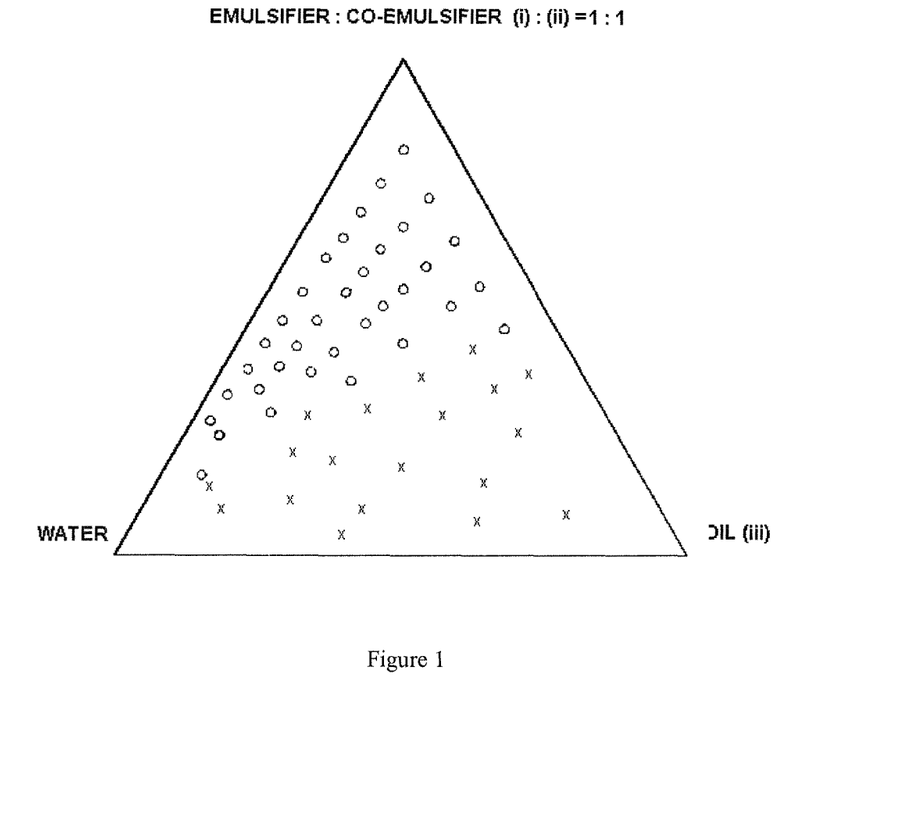
FIGS. 1, 2, 3, and 4 are phase diagrams that illustrate the results of experiments carried out to test the effect of adding water to different compositions of emulsifier, coemulsifier and oil.
Figure 2:
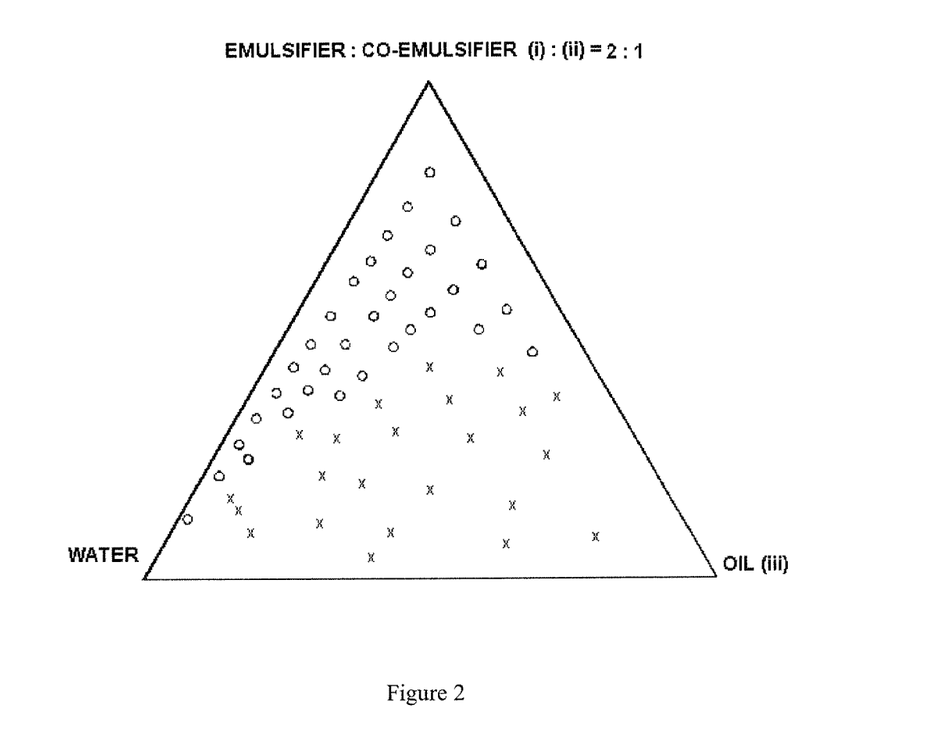
Figure 3:
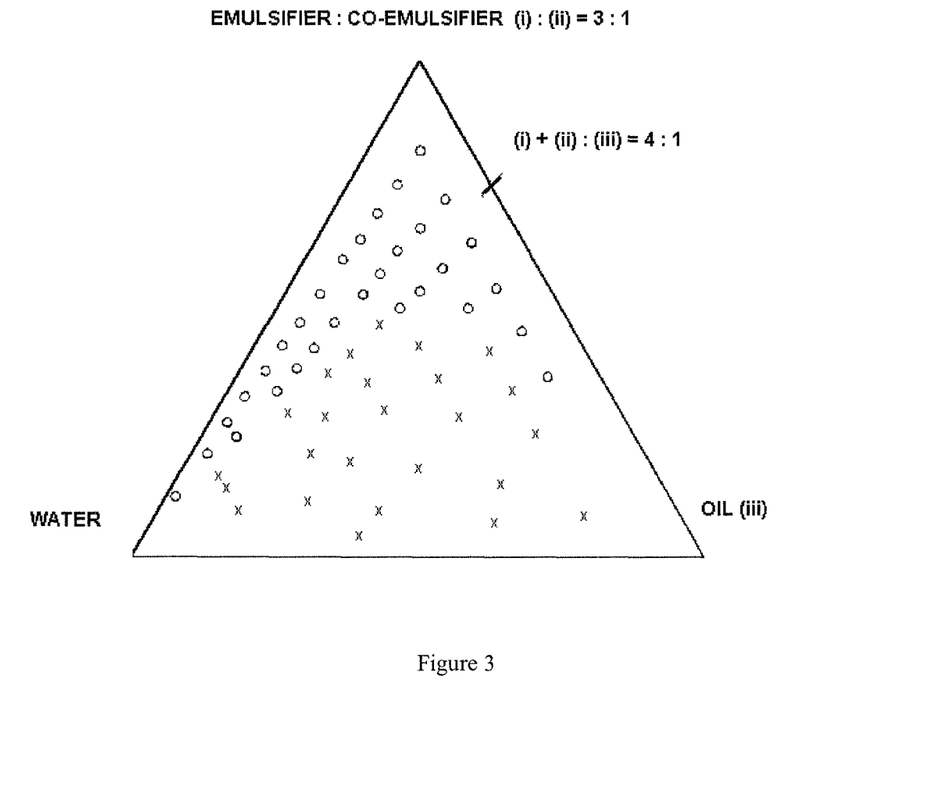
Figure 4:
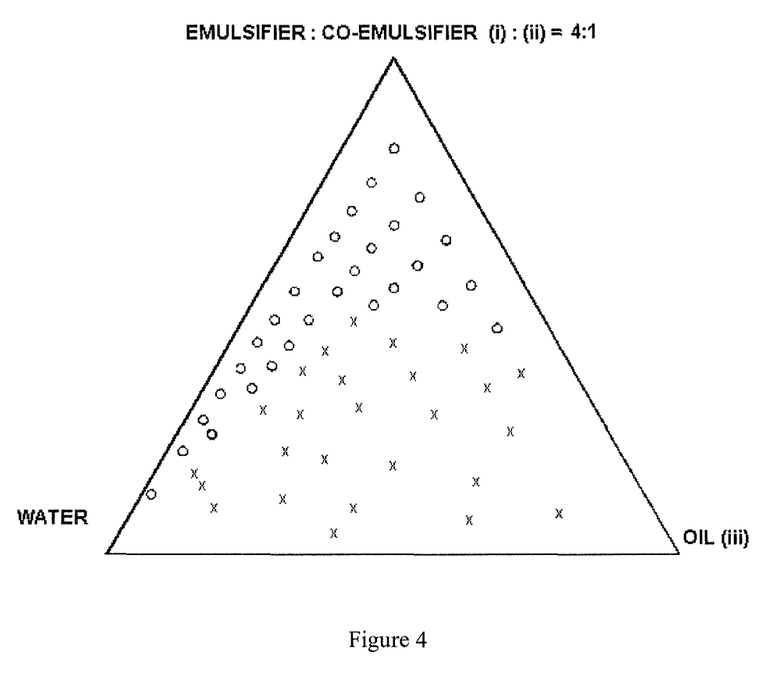

Experiments were carried out with different ratios of emulsifier to coemulsifier. In FIG. 1 the polysorbate 80 Polysorbate 80 (polyoxyethylene 20 sorbitan monooleate) to glyceryl caprylate (Imwitor 308® (glyceryl mono caprylate)) (i.e. (i): (ii)) ratio was 1:1; in FIG. 2 the ratio was 2:1; in FIG. 3 the ratio was 3:1; and in FIG. 4 the ratio was 4:1.

The proportions of emulsifier and coemulsifier are fixed relative to one another in each figure and experiments are carried out with samples having varying proportions of total emulsifier (i.e. Polysorbate 80 (polyoxyethylene 20 sorbitan monooleate) plus Imwitor 308® (glyceryl mono caprylate))) and oil (Mygliol 812® (caprylic/capric triglyceride)).

Water was titrated into each sample and the resulting mixture was assessed to determine whether a microemulsion or a non-microemulsion was formed. The formation of microemulsion was identified according to transparency and stability of the system. The results are shown on the diagrams.

From the figures it is clear that stable microemulsions do not form throughout the ranges depicted by phase diagrams The parts of diagrams where microemulsions are formed are designated by circles, while the parts where emulsions were formed are designated by crosses. The prepared mixtures were assessed to determine whether microemulsions were formed.

The diagrams show that in all cases, with the preferred levels of total emulsifier to oil (i.e. a ratio of at least 1:1) a microemulsion can be formed with varying amounts of water including with very high amounts of water.

EXAMPLES

The examples which follow illustrate the invention (but do not limit it in any way). The findings of the examples was that the use of SMEDDS according to the invention significantly improved the solubility of candesartan cilexetil compared to the marketed candesartan cilexetil formulation (Atacand® (candesartan cilexetil)). It also improved the absorption of candesartan across the intestine compared to the marketed candesartan cilexetil formulation (Atacand® (candesartan cilexetil)).

The use of solid state surfactant based systems were also found to enhance the solubility of a NSAID, celecoxib more than threefold.

Example 1

Preparation of Microemulsions:

| Ingredients | ME 1 | ME 2 | SMEDDS |
|---|---|---|---|
| Miglyol 812 ® | 36.00% | 11.70% | 20.00% |
| Polysorbate 80 | 40.73% | 34.88% | 60.00% |
| Imwitor 308 ® | 13.57% | 11.62% | 20.00% |
| Water | 9.70% | 41.80% | — |

Procedure: Imwitor 308® (glyceryl mono caprylate)) (co-emulsifier) was heated in water bath at 40° C., then Polysorbate 80 (polyoxyethylene 20 sorbitan monooleate) (emulsifier) was added. Both ingredients were mixed thoroughly. Mixture was allowed to cool and then Miglyol 812® (caprylic/capric triglyceride) (oil phase) and water were added. Microemulsions were formed spontaneously after stirring. Self microemulsifying system (SMEDDS) was prepared in the same way but without water. These microemulsions and SMEDDS were used in the following examples.

Example 2

Conversion of Candesartan Cilexetil Microemulsion into Solid State by Adsorption on Colloidal Silicon Dioxide

| Ingredients | Example 2a | Example 2b |
|---|---|---|
| Candesartan cilexetil | 16 mg | 16 mg |
| Microemulsion ME 1 | 114 mg | |
| Microemulsion ME 2 | | 114 mg |
| Colloidal silicon dioxide | 70 mg | 70 mg |

Procedure: Candesartan cilexetil was dispersed homogenously in microemulsion system. This dispersion was slowly added to colloidal silicon dioxide during continuous vigorous mixing to obtain a free flowing powder. Powder was filled in hard capsules.

Example 3

Conversion of Candesartan Cilexetil Microemulsion into Solid State by Incorporation in Polyethylene Glycol Dispersion

| Ingredients | Example 3 |
|---|---|
| Candesartan cilexetil | 16 mg |
| SMEDDS | 84 mg |
| Polyethylene glycol 6000 | 100 mg |

Procedure: Polyethylene glycol 6000 was melted in water bath at 65° C. Candesartan cilexetil was dispersed homogenously in self microemulsifying system. This dispersion was mixed with melted polyethylene glycol 6000. The obtained mixture was rapidly solidified in ice bath. Solidified composition was pulverized and sieved. Granulate was filled in hard capsules. The crystal structure (form I) of candesartan cilexetil in the granulate was detected by powder X-ray diffraction (XRD).

Example 4

Preparation of Solid State Spray Dried Microemulsion with Different Solid Supports

| Ingredients | Ex. 4a | Ex. 4b | Ex. 4c | Ex. 4d | Ex. 4e | Ex. 4f |
|---|---|---|---|---|---|---|
| SMEDDS | 30 mg | 24 g | 20 mg | 30 mg | 24 mg | 20 mg |
| Lactose | 30 mg | 36 g | 40 mg | — | — | — |
| Polyvinylpyrrolidone | — | — | — | 30 mg | 36 mg | 40 mg |
| Water | 200 mg | 200 mg | 200 mg | 200 mg | 200 mg | 200 mg |

| Ingredients | Ex. 4g | Ex. 4h | Ex. 4i | Ex. 4j | Ex. 4k | Ex. 4l |
|---|---|---|---|---|---|---|
| SMEDDS | 30 mg | 24 g | 20 mg | 30 mg | 24 mg | 20 mg |
| Hydroxpropycellulose | 30 mg | 36 g | 40 mg | — | — | — |
| Colloidal silicon dioxide | — | — | — | 30 mg | 36 mg | 40 mg |
| Water | 200 mg | 200 mg | 200 mg | 200 mg | 200 mg | 200 mg |

Procedure: Solid support was dissolved or dispersed in water. This dispersion was mixed together with self microemulsifying system. The obtained dispersion was spray dried in a spray drying system.

Example 5

Conversion of Candesartan Cilexetil Microemulsion into Solid State by Spray Drying

| Ingredients | Example 5a | Example 5b | Example 5c | Example 5d |
|---|---|---|---|---|
| Candesartan cilexetil | 16 mg | 16 mg | 16 mg | 32 mg |
| SMEDDS | 74 mg | 92 mg | 123 mg | 67.2 mg |
| Polyvinylpyrrolidone | 110 mg | — | — | 100.8 mg |
| Colloidal silicon dioxide | — | 92 mg | 61 mg | — |
| Water | 736 mg | 736 mg | 736 mg | 736 mg |

Procedure: Candesartan cilexetil was dispersed homogenously in self microemulsifying system. Polyvinylpyrrolidone was dissolved in water, while colloidal silicon dioxide was dispersed in water. Both dispersion were mixed together. The obtained dispersion was spray dried in a spray drying system. Powder was filled in hard capsules or compressed in tablets. The crystal structure (form I) of candesartan cilexetil in the granulate was detected by powder X-ray diffraction (XRD).

Example 6

Conversion of candesartan cilexetil microemulsion into solid state by stabilization of individual phases with colloidal silicon dioxide and hydrophobic colloidal silicon dioxide

| Ingredients | Example 6a | Example 6b |
|---|---|---|
| Candesartan cilexetil | 16 mg | 16 mg |
| Miglyol 812 ® | 45 mg | 14 mg |
| Hydrophobic colloidal silicon dioxide | 12 mg | 50 mg |
| Polysorbate 80 | 53 mg | 42 mg |
| Imwitor 308 ® | 17 mg | 14 mg |
| Water | 12 mg | 50 mg |
| Colloidal silicon dioxide | 45 mg | 14 mg |

Procedure Imqitor 308® (coemulsifier) was heated in water bath at 40° C., then Polysorbate 80 (polyoxyethylene 20 sorbitan monooleate)(emulsifier) was added. Both ingredients were mixed thoroughly. Emulsifier mixture was allowed to cool. Candesartan cilexetil was dispersed homogenously in emulsifier mixture. Miglyol 812® (caprvlic/capric triqlyceride)(oil phase) was adsorbed on hydrophobic colloidal silicon dioxide and water was adsorbed on colloidal silicon dioxide. Emulsifier mixture, adsorbed oil phase and adsorbed water phase were mixed to obtain a free flowing powder. Powder was filled in hard capsules.

Example 7

Solubility of Candesartan Cilexetil in Solid State Emulsion Systems

| Sample | Sample weight | Solubility (µg/ml) |
|---|---|---|
| Candesartan cilexetil | 50 mg | <0.1 |
| Example 2a | 400 mg (200 mg) | 5.6 (2.3) |
| Example 2b | 200 mg | 2.5 |
| Example 3 | 400 mg | 32.4 |
| Example 5a | 400 mg | 58.8 |
| Example 5b | 400 mg | 1.3 |
| Example 5c | 400 mg | 8.1 |
| Example 6a | 400 mg (200 mg) | 8.6 (3.8) |
| Example 6b | 200 mg | 1.3 |

The solubility of candesartan cilexetil in water was studied at room temperature. Water dispersion (100 ml) of the sample in the laboratory beaker was mixed on the magnetic stirrer for 60 minutes. Afterwards, the part of the dispersion was taken from the beaker, filtered through the 0.45 µm filter and the concentration of candesartan cilexetil was determined by HPLC.

One can see that the solubility of candesartan cilexetil from solid state surfactant based systems is influenced by the sample weight, at 400 mg the solubility is about 2.5-fold higher compared to the 200 mg. Therefore, taking into an account the normalization of results obtained for Examples 2b and 6b to 400 mg, it can be concluded that particular high solubility of candesartan cilexetil was obtained for Examples 3 and 5a, demonstrating that the spray-drying of candesartan cilexetil SMEDDS on polyvinylpyrrolidone, and incorporation of candesartan cilexetil SMEDDS in polyethylene glycol dispersion are particularly advantageous.

Example 8

Comparative solubility of candesartan cilexetil from the formulation prepared according to Example 3 and marketed candesartan cilexetil formulation Atacand® (candesartan dilexetil) in in vivo relevant medium Ringer buffer pH 6.85.

| Sample | Solubility (µg/ml) |
|---|---|
| Example 3 | 104.2 |
| Atacand ® 32 mg | 12.3 |

The solubility of candesartan cilexetil was studied in Ringer buffer pH 6.85 containing 0.5 mM Lecithin and 2.5 mM sodium taurocholate, which simulates the conditions in the small intestine, a primary site of candesartan cilexetil absorption. An amount of formulation prepared according to Example 3 corresponding to 32 mg of candesartan cilexetil or a marketed candesartan cilexetil tablet Atacand® (candesartan dilexetil) containing 32 mg of candesartan cilexetil was placed in 100 ml of above described medium and stirred on the magnetic stirrer for 60 minutes. Afterwards, the part of the dispersion was taken, filtered through the 0.45 µm filter and the concentration of candesartan cilexetil was determined by HPLC. Results clearly show markedly increased solubility of candesartan cilexetil in the novel formulation compared to the marketed formulation.

Example 9

Comparative intestinal absorption of candesartan from the formulation prepared according to Example 3 and marketed candesartan cilexetil formulation Atacand® (candesartan dilexetil).

| Formulation | Absorbed candesartan (nmol) in 60 minutes | Absorbed candesartan (nmol) in 120 minutes |
| --- | --- | --- |
| Example 3 | 0.90 | 3.0 |
| Atacand ® 32 mg | 0.40 | 2.1 |

The intestinal absorption of candesartan was studied in validated in vitro system (side-by-side diffusion chambers), a well accepted model for studying intestinal drug absorption. Excised rat small intestine was used as a model for the intestinal tissue. An amount of formulation prepared according to Example 3 corresponding to 32 mg of candesartan cilexetil or a marketed candesartan cilexetil tablet Atacand® (ccandesartan cilexetil) containing 32 mg of candesartan cilexetil was dispersed in 100 ml of the physiologically relevant intestinal solution (pH=6.8). The dispersions were then placed on the mucosal (donor) side of the intestine and after 60 and 120 minutes samples were taken from the serosal (acceptor) side and the concentrations of absorbed candesartan were determined by HPLC. Results show that the absorption of candesartan from the novel candesartan cilexetil formulation is better compared to the marketed formulation.

Example 10

Conversion of Solid State Spray Dried Candesartan Cilexetil Microemulsion Into Tablets

| Ingredients | Example 10a | Example 10b | Example 10c |
| --- | --- | --- | --- |
| Example 5d | 200 mg | 200 mg | 200 mg |
| Microcrystalline cellulose | 76 mg | — | 136 mg |
| Crospovidone | 60 mg | — | — |
| Mannitol | — | 49 mg | — |
| Sorbitol | — | 49 mg | — |
| Absolute ethanol | 26 mg | 16 mg | 35 mg |

| Ingredients | Example 10d | Example 10e | Example 10f |
| --- | --- | --- | --- |
| Example 10a | 336 mg | — | — |
| Example 10b | — | 298 mg | — |
| Example 10c | — | — | 336 mg |
| Crospovidone | 60 mg | — | — |
| Mannitol | — | 49 mg | — |
| Sorbitol | — | 49 mg | — |
| Hypromellose | — | — | 60 mg |
| Magnesium stearate | 2 mg | 2 mg | 2 mg |
| Colloidal silicon dioxide | 2 mg | 2 mg | 2 mg |

Procedure: Solid state spray dried candesartan cilexetil microemulsion (Example 4d) was mixed with microcrystalline cellulose, crospovidone, mannitol or sorbitol according to Examples 10a, 10b and 10c and granulated with absolute ethanol. Granulate was sieved through 0.700 mm sieve and dried.

Dried granulate was mixed with crospovidone, mannitol, sorbitol, hypromellose, magnesium stearate and colloidal silicon dioxide according to Examples 10d, 10e and 10f. Mixtures were compressed in tablets.

Example 11

Conversion of Celecoxib Microemulsion into Solid State by Adsorption on Colloidal Silicon Dioxide

| Ingredients | Example 11a | Example 11b |
| --- | --- | --- |
| Celecoxib | 100 mg | 100 mg |
| Microemulsion ME 1 | 100 mg | |
| Microemulsion ME 2 | | 100 mg |
| Colloidal silicon dioxide | 60 mg | 60 mg |

Procedure: Celecoxib was dispersed homogenously in microemulsion system. This dispersion was slowly added to colloidal silicon dioxide during continuous vigorous mixing to obtain a free flowing powder. Powder was filled in hard capsules.

Example 12

Conversion of celecoxib microemulsion into solid state by stabilization of individual phases with colloidal silicon dioxide and hydrophobic colloidal silicon dioxide

| Ingredients | Example 12a | Example 12b |
| --- | --- | --- |
| Celecoxib | 100 mg | 100 mg |
| Miglyol 812 ® | 40 mg | 12 mg |
| Hydrophobic colloidal silicon dioxide | 10 mg | 43 mg |
| Polysorbate 80 | 45 mg | 38 mg |
| Imwitor 308 ® | 15 mg | 12 mg |
| Voda | 10 mg | 43 mg |
| Colloidal silicon dioxide | 40 mg | 12 mg |

Procedure: Imwitor 308® (coemulsifier; glyceryl mono caprylate) was heated in water bath at 40° C., then Polysorbate 80 (emulsifier; polyoxyethylene 20 sorbitan monooleate) was added. Both ingredients were mixed thoroughly. Emulsifier mixture was allowed to cool. Celecoxib was dispersed homogenously in emulsifier mixture. Miglyol 812® (oil phase; caprylic/capric triqlyceride) was adsorbed on hydrophobic colloidal silicon dioxide and water was adsorbed on colloidal silicon dioxide. Emulsifier mixture, adsorbed oil phase an adsorbed water phase were mixed to obtain a free flowing powder. Powder was filled in hard capsules.

Example 13

Conversion of Celecoxib Microemulsion into Solid State by Spray Drying

| Ingredients | Example 13 |
| --- | --- |
| Celecoxib | 100 mg |
| SMEDDS | 64 mg |

-continued

| Ingredients | Example 13 |
|---|---|
| Polyvinylpyrrolidone | 96 mg |
| Water | 640 mg |

Procedure: Celecoxib was dispersed homogenously in self microemulsifying system. Polyvinylpyrrolidone was dissolved in water. Both dispersion were mixed together. The obtained dispersion was spray dried in a spray drying system. Powder was filled in hard capsules.

Example 14

Solubility of Celecoxib in Solid State Emulsion Systems

| Sample | Sample weight | Solubility (μg/ml) |
|---|---|---|
| Celecoxib | 100 mg, ultrasound | 0.3 |
| Example 11a | 100 mg | 2.8 |
| Example 11b | 100 mg | 0.9 |
| Example 12a | 100 mg | 4.9 |
| Example 12b | 100 mg | 3.8 |
| Example 13 | 100 mg | 4.9 |

The solubility of celecoxib in water was determined with the same procedure as described in Example 7.

Example 15

Conversion of Microemulsion into Solid State by Spray Drying

| Ingredients | Example 15a | Example 15b | Example 15c |
|---|---|---|---|
| Sirolimus | 2.0 mg | — | — |
| Lercanidipine HCl | — | 20.0 mg | — |
| Eprosartan mesylate | — | — | 300.0 mg |
| SMEDDS | 29.2 mg | 32.0 mg | 120.0 mg |
| Polyvinylpyrrolidone | 43.8 mg | 48.0 mg | 180.0 mg |
| Water | 276.0 mg | 368.0 mg | 2208.0 mg |

Procedure: Active ingredient (which was sirolimus, lercanidipine HCl and eprosartan mesylate in examples 15a, b and c respectively) was dispersed homogenously in self microemulsifying system, while polyvinylpyrrolidone was dissolved in water. Both dispersion were mixed together. The obtained dispersion was spray dried in a spray drying system. Powder was filled in hard capsules or compressed in tablets.

Example 16

Conversion of Solid State Spray Dried Microemulsion into Tablets

| Ingredients | Example 16a | Example 16b | Example 16c |
|---|---|---|---|
| Example 15a | 75.00 mg | — | — |
| Example 15b | — | 100.00 mg | — |
| Example 15c | — | — | 600.00 mg |
| Microcrystalline cellulose | 28.50 mg | 68.00 mg | 228.00 mg |
| Crospovidone | 22.50 mg | — | 180.00 mg |
| Absolute ethanol | 9.75 mg | 17.50 mg | 78.00 mg |

| Ingredients | Example 16d | Example 16e | Example 16f |
|---|---|---|---|
| Example 16a | 126.00 mg | — | — |
| Example 16b | — | 168.00 mg | — |
| Example 16c | — | — | 1008.00 mg |
| Crospovidone | 22.50 mg | — | 180.00 mg |
| Hypromellose | — | 30.00 mg | — |
| Magnesium stearate | 0.75 mg | 1.00 mg | 6.00 mg |
| Colloidal silicon dioxide | 0.75 mg | 1.00 mg | 6.00 mg |

Procedure: Solid state spray dried microemulsions (Example 15a, 15b, 15c) was mixed with microcrystalline cellulose and crospovidone according to Examples 16a, 16b and 16c and granulated with absolute ethanol. Granulate was sieved through 0.700 mm sieve and dried. Crospovidone is an insoluble rapidly swellable crosslinked polymer of N-vinyl-2-pyrriolidone that acts as a disintegrant.

Dried granulate was mixed with crospovidone, hypromellose, magnesium stearate and colloidal silicon dioxide according to Examples 16d, 16e and 16f. Mixtures were compressed in immediate release sirolimus and eprosartan mesylate tablets or lercanidipine controlled release tablets. Hypromellose is a semisynthetic inert, viscoelastic polymer, otherwise known as hydroxypropyl methyl cellulose.

The invention claimed is:

1. A self-microemulsifying drug delivery system consisting of:
   (i) a polyoxyethylene sorbitan fatty acid ester emulsifier;
   (ii) a co-emulsifier selected from glyceryl mono- or di-fatty acid esters of $C_6$-$C_{18}$ fatty acids; and
   (iii) an oil, selected from $C_6$-$C_{12}$ fatty acid triglycerides;
   wherein the polyoxyethylene sorbitan fatty acid ester emulsifier (i) and co-emulsifier (ii) are present in a ratio by weight of between 1:1 and 4:1 and
   the emulsifier and co-emulsifier, (i)+(ii), and oil (iii) are present in a ratio by weight of between 4:1 and 10 000:1; and wherein said drug delivery system is stable on addition of any amount of water.

2. A self-microemulsifying drug delivery system according to claim 1, wherein the emulsifier (i) is a polysorbate.

3. The self-microemulsifying drug delivery system of claim 2, wherein the polysorbate is Polysorbate 80.

4. A self-microemulsifying drug delivery system according to claim 1, wherein the ratios are selected from the group of ratios consisting of:
   the polyoxyethylene sorbitan fatty acid ester emulsifier (i) and co-emulsifier (ii) are present in a ratio by weight of about 1:1, about 2:1, about 2.5:1, about 3:1, about 3.5:1 and about 4:1;
   the ratio by weight of emulsifier and co-emulsifier, (i)+(ii), to oil (iii), is in the range selected from the group consisting of about 4:1 to 1000:1, about 4:1 to 100:1, and about 5:1 to 40:1; and
   the ratio of coemulsifier (ii) to oil (iii) is selected from the group consisting of at least 1.5:1, at least 2:1, and at least 3:1.

5. A self-microemulsifying drug delivery system according to claim 1, wherein the polyoxyethylene sorbitan fatty acid ester emulsifier (i) and co-emulsifier (ii) are present in a ratio by weight of between 2.5:1 and 3.5:1.

6. A self-microemulsifying drug delivery system according to claim 1, wherein the co-emulsifier is selected from glyceryl mono- or di-fatty acid esters of $C_6$-$C_{12}$ fatty acids.

7. The self-microemulsifying drug delivery system according to claim 6, wherein the co-emulsifier is glyceryl caprylate.

8. A self-microemulsifying drug delivery system according to claim 1, wherein the oil is a caprylic or a capric triglyceride oil.

* * * * *